United States Patent

Koppe et al.

[11] Patent Number: 5,978,439
[45] Date of Patent: Nov. 2, 1999

[54] X-RAY IMAGING METHOD INVOLVING A SERIES OF IMAGES FROM DIFFERENT PERSPECTIVES

[75] Inventors: Reiner H. Koppe, Hamburg; Erhard P.A. Klotz, Neumünster, both of Germany; John Op De Beek, Son, Netherlands

[73] Assignee: U.S. Philips Corporation, New York, N.Y.

[21] Appl. No.: 09/019,501

[22] Filed: Feb. 5, 1998

[30] Foreign Application Priority Data

Feb. 14, 1997 [DE] Germany ............................ 197 05 599

[51] Int. Cl.$^6$ ........................................................ A61B 6/03
[52] U.S. Cl. ................................................ 378/8; 378/901
[58] Field of Search .................................... 378/4, 8, 901; 382/131

[56] References Cited

U.S. PATENT DOCUMENTS 5,150,427   9/1992   Frazee et al. ............................ 382/48
5,852,646  12/1998   Klotz et al. ............................... 378/8

FOREIGN PATENT DOCUMENTS 0041749   12/1981   European Pat. Off. .
0492896A2  1/1992   European Pat. Off. .

*Primary Examiner*—David Vernon Bruce
*Attorney, Agent, or Firm*—Dwight H. Renfrew

[57] ABSTRACT

The invention relates to a method which enables distributed or dilute structures, for example a vascular system filled with a contrast medium, to be reproduced in a synthetic projection image which reproduces the parts of the vascular system which are situated in a selectable sub-volume more clearly than the X-ray images, formed from different perspectives, wherefrom the projection image is derived. The voxel image values associated with the voxels of the sub-volume are first determined and from these voxel image values there is calculated a synthetic projection image in which the selected sub-volume is reproduced.

12 Claims, 3 Drawing Sheets

X-RAY IMAGING METHOD INVOLVING A SERIES OF IMAGES FROM DIFFERENT PERSPECTIVES

BACKGROUND OF THE INVENTION

1. Field of the Invention

The invention relates to an X-ray imaging method in which a series of two-dimensional X-ray images is formed and digitally stored, an object to be examined which is situated in an examination zone being projected onto an X-ray image pick-up device from different perspectives and voxel image values being reconstructed from the image values of the X-ray images for voxels present in the examination zone, and also relates to the device for carrying out the method.

2. Description of Related Art

A method and a device of the kind set forth are known from EP-A-492 896. Therein, X-ray images are formed from perspectives which differ 180° (or more). Nevertheless, the data thus acquired is not complete because the X-ray beam does not cover the edges of the object to be examined so that some X-ray images contain structures of the object to be examined which are absent in other X-ray images.

In order to reconstruct the voxel image values (herein voxels are to be understood to mean volume elements of the examination zone) use is made of an iterative method in which, in addition to the data of the X-ray images, a priori information concerning the outer contour of the object to be examined is taken up in the reconstruction. This method requires a large amount of calculation work on the one hand and, on the other hand, is not suitable for the imaging of the vascular system because it is a prerequisite that the vascular system is filled with a contrast medium in all X-ray images. This condition can hardly be satisfied in practice.

SUMMARY OF THE INVENTION

It is an object of the present invention to provide a method which is suitable for the reconstruction of "dilute structures", i.e. structures which, like a vascular system filled with a contrast medium, occupy only a small part of the surface area of the X-ray images and have an X-ray absorptivity which is substantially higher than that of the areas surrounding these structures. This method is intended to produce images which, for a small part of the examination zone, reproduce the dilute structures more clearly and with a higher contrast than the original X-ray images.

On the basis of a method of the kind set forth this object is achieved by taking the following steps:

a) selecting a sub-volume of the examination zone, b) deriving voxel image values which are specific of the voxels of the sub-volume from the image values of the pixels on which the voxel is mapped in the individual X-ray images, c) projecting the image values into at least one synthetic projection image.

The invention enables the reproduction of distributed structures, for example a vascular system filled with a contrast medium, in a synthetic projection image which reproduces the parts of the vascular system which are present in a selectable sub-volume more clearly than the X-ray images which are formed from different perspectives and are used to form this projection image. According to this method, first the voxel image values associated with the voxels of the sub-volume are determined and from these voxel image values there is calculated a synthetic projection image in which the selected sub-volume is imaged.

The invention is based on the following considerations. The selection of a sub-volume of the examination zone first defines the area in which the dilute structures, or the vascular system, are to be reproduced with a higher quality. The smaller this area, the shorter the calculation time will be and the more distinct the differences with respect to the original X-ray images will be. Subsequently, the voxel image values associated with the voxels of the selected sub-volume are reconstructed. Each of these voxels influences the image values of one or more pixels in each of the X-ray images (herein a pixel is to be understood to mean an image element of an image or X-ray image).

The image values of these pixels are also influenced by voxels which are situated outside the sub-volume in the examination zone, but such an exterior voxel influences in one X-ray image only the image value of the same pixel as a given voxel within the sub-volume. In the other X-ray images the exterior voxel influences the image values of pixels other than the voxel present within the sub-volume. Because the voxel image value of a voxel within the sub-volume, however, is derived from the image values of its associated pixels in a large number of X-ray images, the voxel situated outside the sub-volume has a small effect only on the voxel image value assigned to a voxel within the sub-volume. So far the circumstances are similar to those in the case of a conventional X-ray slice image in which voxels situated outside a slice are reproduced only in "blurred" or unsharp form in a slice image.

Subsequently, a synthetic projection image is calculated in which the voxels of the selected sub-volume, and only these voxels, are projected. The projection image thus formed, which may have the same or other geometrical parameters as one of the X-ray images, therefore, essentially reproduces only structures from the selected sub-volume. Consequently, it reproduces the vascular system within the sub-volume more clearly than the original X-ray images, because the X-ray images also contain a sharp image of the vascular system outside the sub-volume which interferes with the interpretation of the vascular structure of interest in the sub-volume.

For the method according to the invention it may be necessary to store the voxel image values determined for the sub-volume before a projection image (or several projection images) is formed therefrom. When the sub-volume is comparatively large, it may contain large numbers of voxels so that a high storage capacity is required for the voxel image values.

The storage of all voxel image values from the selected sub-volume, however, can be dispensed with according to a further preferred version of the method of the invention in which the following sequence of processing steps is executed:

a) selecting a voxel from the sub-volume, b) determining the pixels associated with this voxel in the X-ray images, c) deriving a voxel image value which is specific of this voxel from the image values associated with these pixels, d) projecting the voxel into at least one synthetic projection image, e) repeating the steps a–d for other voxels of the sub-volume.

After the step d), in which the voxel is projected into one or more synthetic projection images, the voxel image value of this voxel will no longer be required for the projection image (images), so that the voxel image value need not (or no longer) be stored. It is only necessary to store the voxel image value of the relevant voxel being processed.

In a preferred version of the invention, the voxel image value which is specific of a voxel of the sub-volume is derived by averaging from the image values of the pixels associated with the voxel in the individual X-ray images. This enables very simple calculation of the voxel image value from the image values of the pixels associated with the voxel. Voxel image values of voxels in which a vessel filled with contrast medium is present are then practically perfectly reproduced, because the image values of the pixels in all X-ray images are significantly influenced by this voxel. However, voxels representing the image background (low absorption) could be falsely reconstructed if voxels of high absorption are also projected onto the associated pixels in the individual X-ray images. However, this is not a disturbing effect because contour-less blurring takes place if an adequate number of (for example, 80) images is available.

In a further version of the invention, the voxel image value which is specific of the voxel is derived from the image values of the pixels associated with the voxel in the individual X-ray images by ordering these image values according to magnitude, an image value being selected which has a selectable rank within said order. If the rank within the order of image values is chosen so that it lies between the median value and the image value corresponding to the highest absorption, the diluted structures will be clearly reproduced in the projection images.

In a further version of the invention, in the case of projection of different voxels on a common pixel of the synthetic projection image, the voxel image value of these voxels which corresponds to the lowest absorption of the X-rays during the X-ray exposure is assigned to the pixel. As a result, the image value of a pixel in the synthetic projection image is determined by the voxel having the lowest absorption. This is usually a voxel which reproduces a diluted structure, so that the dilute structures will be clearly reproduced in the synthetic projection images.

In a further version of the invention, the synthetic projection image is at least partly subjected to a non-linear filtering operation during which all image values beyond a limit value are set, for example to a maximum value or a minimum value whereas the remaining image values are spread out across the range between the minimum value and the maximum value. When the limit value is suitably chosen, the image background (i.e. the image areas in which no dilute structure is reproduced) can be made to disappear, for example in that it is reproduced in white in the projection image whereas the dilute structures (vessels) appear in black in this image.

In a further version of the invention, which is intended to reproduce the vascular system of a patient, a contrast medium is injected, prior to the formation of the X-ray images, so as to form a series of X-ray images reproducing the patient's vascular system filled with contrast medium. The contrast medium injection enables the vessels to be imaged as a dilute structure. In a further version yet, the X-ray images may be formed by subtraction of a respective pair of X-ray images which reproduce the examination zone from the same perspective, however, with and without a contrast medium, respectively. The X-ray images then correspond to subtraction angography in which the image background is substantially eliminated by the subtraction.

In a further version of the invention, the image pick-up device is moved along an arc of circle during the formation of the X-ray images. The movement of the image pick-up device along an arc of circle which encloses the examination zone can be very simply implemented.

A device for carrying out the method according to the invention includes a first imaging device which includes an X-ray source and an X-ray image pick-up device which are adjustable relative to an object to be examined in order to form a series of two-dimensional X-ray images in which the object to be examined is projected onto the X-ray image pick-up device from different perspectives, which device also includes means for storing the X-ray images and programmable image processing means which are programmed in such a manner that the following image processing operations are carried out:

a) selecting a sub-volume of the examination zone, b) deriving voxel image values which are specific of the voxels of the sub-volume from the image values of the pixels on which the voxel is mapped in the individual X-ray images, c) projecting the image values into at least one synthetic projection image.

A further embodiment of the invention is provided with a C-arm whereto the X-ray source and the X-ray image pick-up device are attached, the C-arm being displaceable to a plurality of exposure positions along a circular path (for example, motorically). A device of this kind can be economically manufactured.

BRIEF DESCRIPTION OF THE DRAWINGS

The invention will be described in detail hereinafter with reference to the drawings. Therein.

DETAILED DESCRIPTION OF THE PREFERRED EMBODIMENTS

Figure 1:
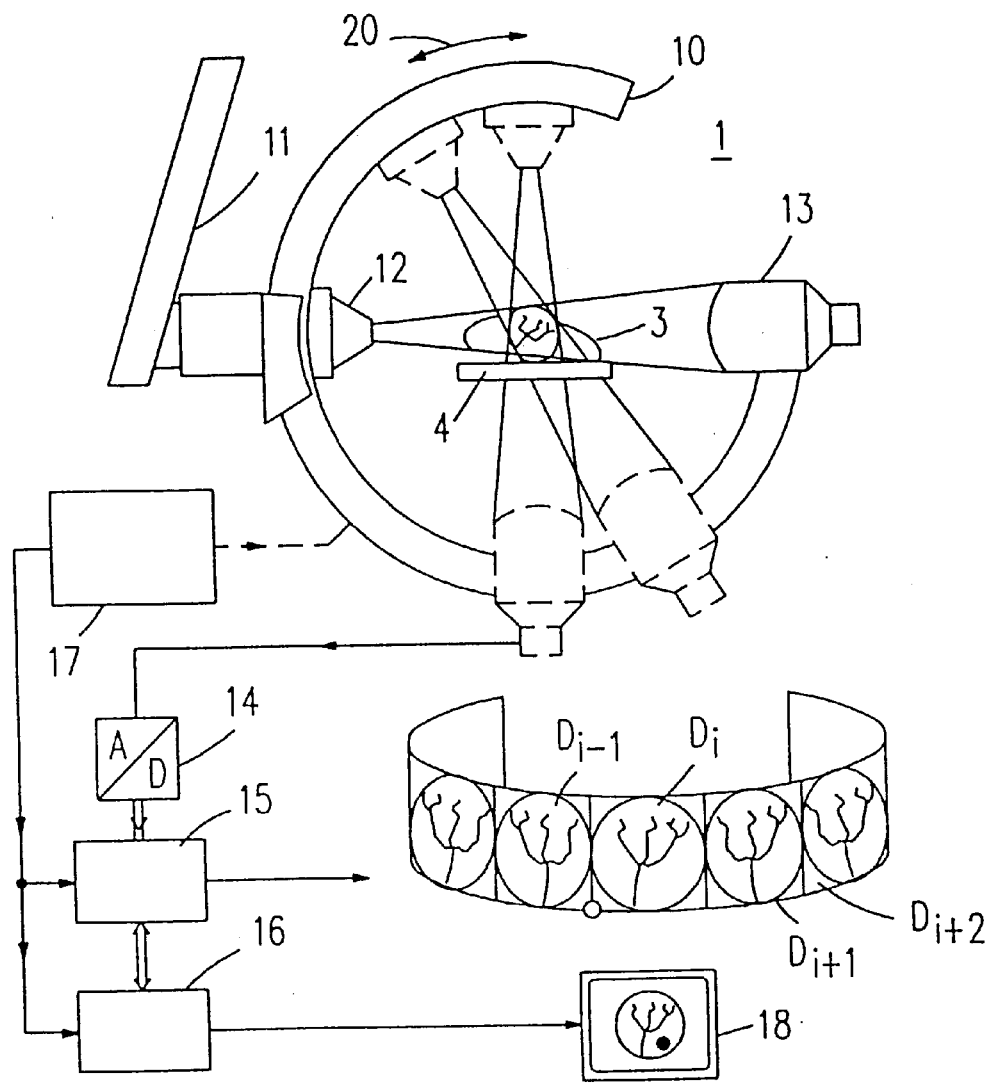
FIG. 1 shows a device for carrying out the method according to the invention.

The reference numeral 1 in FIG. 1 denotes an imaging device which serves to form two-dimensional X-ray images of an object 3 to be examined, for example, a patient who is arranged on a table 4. The imaging device 1 includes an X-ray source 12 and an X-ray image pick-up device 13 which are aligned relative to one another and mounted on an arc of circle 10 (a so-called C-arm) which itself is journalled in a stand 11 which is only partly shown. The C-arm 10 itself can be pivoted about a perpendicular axis on the one hand and be rotated around its center in the direction of the double arrow 20, on the other hand, for example through 180°, by means of a motor drive (not shown). During this motion, a plurality of X-ray images can be formed which reproduce the examination zone 3, 4 from different, reproducible perspectives or angular positions (some of which are denoted by dashed lines) of the image pick-up system 12, 13.

The X-ray image pick-up device 13 may be an X-ray image intensifier whereto a television chain is connected, the output signals thereof being digitized by an analog-to-digital converter 14 so as to be stored in a memory 15, so that at the end of the examination the entire series of X-ray images will have been stored. These X-ray images can be processed by an image processing unit 16. The images formed ( . . . $D_{-1}$, $D_i$, $D_{i+1}$, $D_{i+2}$ . . . ) can be displayed on a monitor 18, either individually or as a series of images. The individual components of the X-ray device are controlled by means of a control unit 17.

Figure 2:
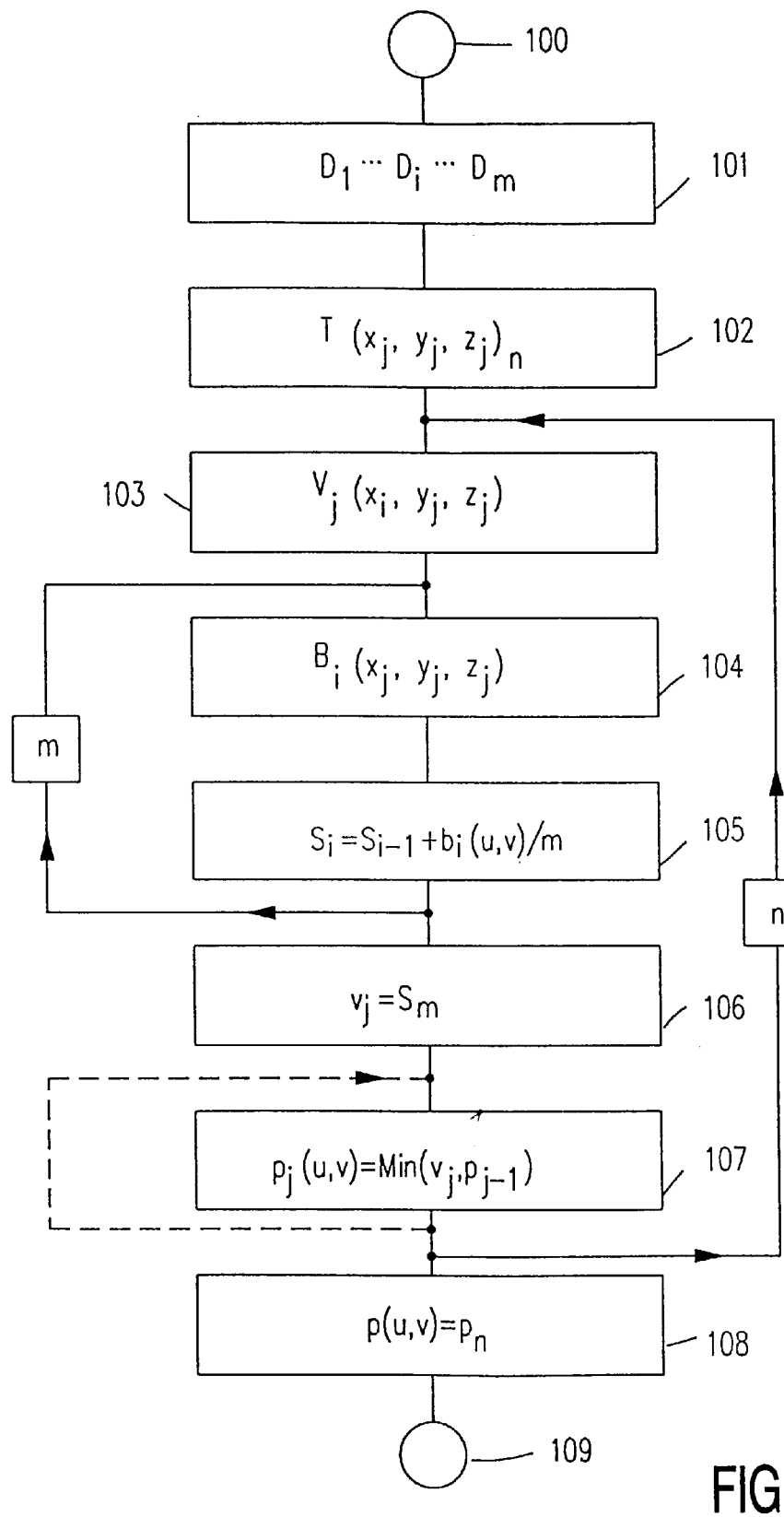
FIG. 2 shows the execution of the individual processing steps of the method according to the invention.

FIG. 2 shows the series of steps executed by the image processing unit 16 or the control unit 17. After the initialization (100), the C-arm 10 is step-wise rotated about its center, after a contrast medium injection, and at the same time a series of m X-ray images (for example, m=100) which reproduce the object to be examined and the blood vessels present therein, filled with a contrast medium, from different perspectives (step 101). It is to be noted that not all parts of the vascular system are filled with contrast medium in all X-ray images. The contrast medium may either not yet have reached the relevant segments or have already left these segments. Even when the imaging system traverses an angular range of 180° or more during the series of exposures, a data set will be acquired which is not adequate for complete reconstruction (for example, by means of a filtered back-projection). Moreover, it may occur in at least some X-ray images that the imaging system does not completely reproduce the object to be examined.

In cases where merely the image of large structures, for example the skull cap, is uniformly superposed on the vascular system in the X-ray images it suffices to form a single series of X-ray images. However, if small structures are irregularly superposed on the image of the vessel, for example the neck vertebrae, it is advisable to perform subtraction angiography. Before or after the contrast medium injection, there is formed a further series of X-ray images which reproduce the same object from the same perspectives but not the vascular system (because either the contrast medium has not yet been injected or the contrast medium has already been distributed to such an extent that it is no longer visible in the image). Subsequently, the corresponding X-ray images of the two series are subtracted from one another, so that merely the vascular system remains because the image background is the same in both series of images. The subtraction images thus formed are also referred to hereinafter as X-ray images.

Moreover, it may be advantageous to form, instead of one series of X-ray images, two series of X-ray images in which the C-arm is each time inclined±α(for example, α=30° ) in relation to a vertical plane. Thus, it is also possible to reproduce structures. which are situated in the plane of the C-arm in one of the two series of X-ray images and, therefore, cannot be reproduced.

During the first processing step 101, moreover, all errors which are due to imperfections of the image pick-up device (for example, display screen curvature and other image defects) or are imposed by the fact that the C-arm is reproducibly distorted by the force of inertia, are corrected.

During the next processing step 102, a sub-volume is selected, which contains a structure which is relevant to the diagnosis, for example an aneurysm. This selection can be interactively performed by the user who marks the areas relevant to the diagnosis, for example by means of a cursor, in two, preferably 90° offset X-ray images of the series of X-ray images. The sub-volume T thus defined may comprise n voxels which are characterized in space by their co-ordinates $x_j$, $y_j$, $z_j (1 \pm j \pm n)$.

During the subsequent step, first one of the voxels $V_j$ of the sub-volume T is selected. For this voxel the pixel $B_i$ which is associated with this voxel in a first X-ray image is determined in step 104, i.e. the pixel on which the relevant voxel is projected during the X-ray exposure. Such determination is possible because on the one hand the position of the voxel is defined by the selection of the sub-volume and on the other hand the position of the imaging system 12, 13 during the formation of the X-ray images is exactly known.

In the step 105 the contribution of the image value $b_i$, associated with the pixel determined, to the voxel image value $v_j$ is determined, for example by calculation of the arithmetical mean value. It may occur that the projection of a voxel covers several pixels in the X-ray image; in that case their image values should be averaged. However, it may also occur that a pixel is only partly covered by the projection of the voxel. This occurrence can be taken into account by way of a corresponding area-wise weighting of the image value of the relevant voxel.

The loop consisting of the steps 104 and 105 is executed m times, the pixels associated with the voxel being determined from each time a different one of the m X-ray images. After the loop 104, 105 has been executed m times, a sum value is obtained which corresponds to the arithmetical mean value of the image values of the pixels which are associated with the voxel in the various X-ray images.

Figure 3:
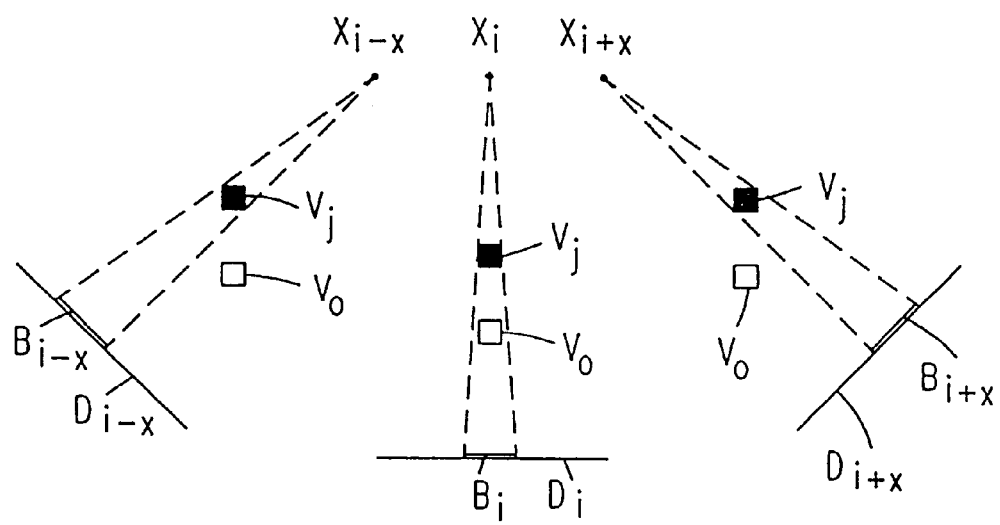
FIG. 3 illustrates the determination of the voxel image values.

These steps are illustrated by FIG. 3. This figure shows the position of the X-ray source ($X_{i-x}$, $X_i$ and $X_{i+x}$) for three X-ray images $D_{i-x}$, $D_i$ and $D_{i+x}$, (where x may be an integer value) and, by way of the X-ray imaging plane $D_{i-x}$, $D_i$ and $D_{i+x}$, the associated position of the image pick-up device. Also shown are the position of the selected voxel Vj and the position of a further voxel $V_o$, which is situated at a distance from the voxel Vj and outside the selected sub-volume. The pixel ($B_{i-x}$, $B_i$ and $B_{i+x}$ on which the voxel is projected in the individual X-ray images is also shown.

It appears that the voxels $V_j$ and $V_O$ are superposed in the X-ray image $D_i$. However, they are not superposed in the other X-ray images. Therefore, practically all image values (except for that or those derived from the image $D_i$) are independent of the voxel $V_o$. Because the voxel image value $v_j$ for the voxel Vj, however, is derived from image values of all X-ray images, the effect of the nuisance voxel $V_0$ remains small overall.

The value obtained after the loop 104, 105 has been executed m times corresponds to the arithmetical mean value which is assigned to the voxel Vj as its voxel image value $v_j$ in the step 106.

Instead of calculating the arithmetical mean value, it is alternatively possible to order the image values associated with the voxel in the individual X-ray images according to magnitude and to select a given value from this order, for example the median value or a different value. However, it is a prerequisite that all image values associated with the voxel $V_j$ in the various X-ray images must then be stored.

Figure 4:
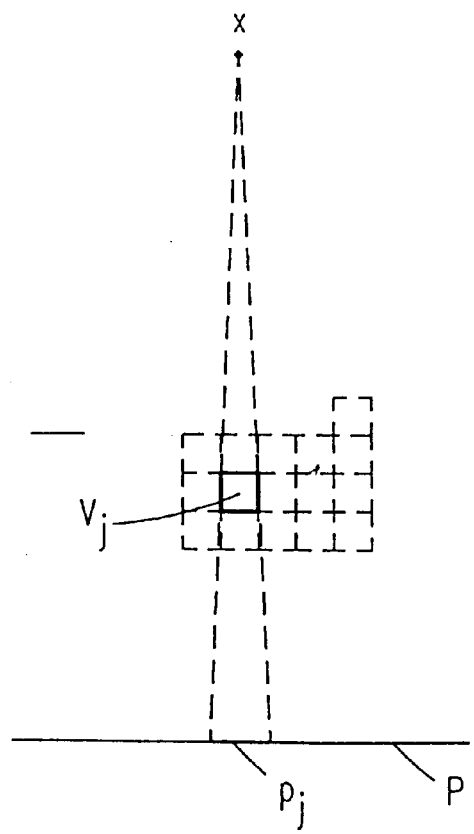
FIG. 4 shows the projection of voxels into a synthetic projection image.

After such reconstruction of the voxel image value $v_j$ associated with a voxel $V_j$, a synthetic projection image (or several projection images) are calculated in which the voxel $V_j$ (and subsequently all other voxels of the sub-volume T) are projected. The projection parameters (i.e. the position of the X-ray source and the image pick-up device on which the projection is based) of this synthetic projection image may be identical to the parameters of one of the X-ray images; however, parameters deviating therefrom may also be used. To this end, in a step 107 the contribution of the voxel $V_j$, whose voxel image value was previously determined, to the synthetic projection image is determined. To this end, in the step 107 first the pixel or pixels is (are) determined on which the voxel $V_j$ is projected in the synthetic projection image (see FIG. 4). For this pixel the contribution made by the voxel image value of the voxel Vj is determined in the same step. First all image values p of the projection image can then be set to a value which corresponds to a maximum X-ray intensity ("white"). For the previously determined pixel $P_j$ of the synthetic projection image, a projection image value is then derived by comparing the voxel image value $v_j$ with an image value $P_{j-1}$ ($p_0$ corresponds to the maximum X-ray intensity) determined for the relevant pixel during the preceding execution. If the voxel image value $v_j$ corresponds to a lower X-ray intensity, the value $p_{j-1}$ is replaced thereby; otherwise, $p_{j-1}$ is retained.

As is indicated by a dashed line, the step 107 is repeated if another one or several further synthetic projection images are calculated.

Subsequently, the loop 103 . . . 107 is executed again for other voxels of the sub-volume T, i.e. as often as there are voxels present in the sub-volume.

It appears that some of the voxels from the sub-volume are projected onto the same pixel $P_j$ on which the voxel $V_j$ was also projected. From the voxel image values $v_j$ associated with all voxels projected onto the pixel $P_j$ that voxel image value which corresponds to the minimum radiation dose is assigned to the pixel in the projection image P by executing the step 107 n times. In this case it may be assumed that, should any of said voxels correspond to a vessel filled with contrast medium, the voxel image value of this vessel will ultimately determine the associated projection image value p. Thus, at step 108 a synthetic projection image P (or several of such images) reproducing the vascular system in the sub-volume T selected in the step 102 will have been calculated after the steps 103 . . . 107 have been executed n times. This synthetic projection image P can be displayed on the monitor 18. This completes the execution of the method (block 109).

It appears from the foregoing that a voxel image value $v_j$ is no longer required after the step 107. Therefore, storage of the voxel image values is not necessary per se. However, if it appears that the projection parameters for the projection image or images were chosen so unattractively that the diagnostically relevant area is not sufficiently clearly reproduced, the voxel image values must be determined again, thus prolonging the reconstruction method. This could be avoided by storing all voxel image values of the selected sub-volume until completion of the method. However, this requires a memory having a capacity which is large enough to store the voxel image values. If the sub-volume T selected during the step 102 is comparatively large, a substantial storage capacity will then be required.

If the method is to be applied to a large (partial) volume, a large amount of calculation work will be required. This amount can be reduced by subdividing the volume into at least two sub-volumes and by performing the method for each sub-volume, the sub-volumes then being projected into a common synthetic projection image.

We claim:

1. An X-ray imaging method in which a series of two-dimensional X-ray mages ($D_1$ . . . $D_i$ . . . $D_n$) is formed and digitally stored, an object to be examined (3, 4) which is situated in an examination zone being projected onto an X-ray image pick-up device from different perspectives and voxel image values ($v_j$) being reconstructed from the image values ($b_i$) of the X-ray images ($D_i$) for voxels ($V_j$) present in the examination zone, characterized in that it includes the following steps:

a) selecting a sub-volume (T) of the examination zone,
    b) deriving voxel image values ($v_j$) which are specific of the voxels ($V_j$) of the sub-volume from the image values ($b_i$) of the pixels ($B_i$) on which the voxel is mapped in the individual X-ray images ($D_i$),
    c) projecting the image values ($v_j$) into at least one synthetic projection image (P).

2. An X-ray imaging method as claimed in claim 1, characterized in that it includes the following processing steps:

a) selecting a voxel ($V_j$) from the sub-volume (T),
    b) determining the pixels ($B_i$) associated with this voxel in the X-ray images ($D_i$),
    c) deriving a voxel image value ($v_j$) which is specific of this voxel ($V_j$) from the image values ($b_i$) associated with these pixels,
    d) projecting the voxel into at least one synthetic projection image,
    e) repeating the steps a–d for other voxels of the sub-volume.

3. An X-ray imaging method as claimed in claim 1, characterized in that the voxel image value ($v_j$) which is specific of a voxel (Vj) of the sub-volume is derived by averaging from the image values ($b_i$) of the pixels ($B_i$) associated with the voxel in the individual X-ray images.

4. An X-ray imaging method as claimed in claim 1, characterized in that the voxel image value ($v_j$) which is specific of the voxel ($V_j$) is derived from the image values ($b_i$) of the pixels ($B_i$) associated with the voxel in the individual X-ray images by ordering these image values according to magnitude their value, an image value being selected which has a selectable rank within said order.

5. An X-ray imaging method as claimed in claim 1, characterized in that in the case of projection of different voxels (V) on a common pixel of the synthetic projection image (P), the voxel image value of these voxels which corresponds to the lowest absorption of the X-rays during the X-ray exposure is assigned to the pixel.

6. An X-ray imaging method as claimed in claim 1, characterized in that the synthetic projection image (P) is at least partly subjected to a non-linear filtering operation during which all image values beyond a limit value are set to a maximum value or a minimum value whereas the remaining image values are spread out across the range between the miniimum value and the maximum value.

7. An X-ray imaging method as claimed in claim 1, characterized in that in order to reproduce the vascular system of a patient, a contrast medium is injected, prior to the formation of the X-ray images, so as to form a series of X-ray images reproducing the patient's vascular system filled with contrast medium.

8. An X-ray imaging method as claimed in claim 7, characterized in that the X-ray images ($D_i$) are formed by subtraction of a respective pair of X-ray images which reproduce the examination zone from the same perspective, however, with and without a contrast medium, respectively.

9. An X-ray imaging method as claimed in claim 1, characterized in that the image pick-up device is moved along an arc of circle, or several arcs of circle with a different angulation (a), during the formation of the X-ray images.

10. An X-ray imaging method as claimed in claim 1, characterized in that in the case of imaging of a rather large partial volume this volume is subdivided into at least two sub-volumes, and that the method is executed for each sub-volume, the sub-volumes being projected into a common synthetic projection image.

11. A device for carrying out the method claimed in claim 1, including a first imaging device (1) which includes an X-ray source (12) and an X-ray image pick-up device (13) which are adjustable relative to an object to be examined in order to form a series of two-dimensional X-ray images ($D_1$ . . . $D_i$ . . . $D_n$) in which the object to be examined is projected onto the X-ray image pick-up device from different perspectives, means (15) for storing the X-ray images and programmable image processing means (16) which are programmed in such a manner that the following image processing operations are carried out:

a) selecting a sub-volume (T) of the examination zone, b) deriving voxel values ($v_j$) which are specific of the voxels ($V_j$) of the sub-volume from the image values ($b_i$) of the pixels ($B_i$) on which the voxel is mapped in the individual X-ray images ($D_i$), c) projecting the image values ($v_j$) into at least one synthetic projection image (P).

12. A device as claimed in claim 11, characterized in that it is provided with a C-arm (10) whereto the X-ray source (12) and the X-ray image pick-up device (13) are attached, the C-arm being displaceable to a plurality of exposure positions along a circular path.

* * * * *